US008496921B2

(12) United States Patent
Wang

(10) Patent No.: US 8,496,921 B2
(45) Date of Patent: Jul. 30, 2013

(54) CONSENSUS INTERFERON VARIANT AND METHODS OF SUPPRESSING VIRAL ACTIVITY

(76) Inventor: Lin Wang, Beijing (CN)

( * ) Notice: Subject to any disclaimer, the term of this patent is extended or adjusted under 35 U.S.C. 154(b) by 0 days.

(21) Appl. No.: 13/555,930

(22) Filed: Jul. 23, 2012

(65) Prior Publication Data

US 2012/0288477 A1 Nov. 15, 2012

Related U.S. Application Data

(63) Continuation of application No. 12/446,519, filed as application No. PCT/CN2009/070607 on Mar. 2, 2009.

(30) Foreign Application Priority Data

Mar. 4, 2008 (CN) .......................... 2008 1 0101309

(51) Int. Cl.
*A61K 38/21* (2006.01)
*A61K 38/00* (2006.01)
*C07K 14/56* (2006.01)

(52) U.S. Cl.
USPC ............................ 424/85.7; 530/351; 514/1.1

(58) Field of Classification Search
None
See application file for complete search history.

(56) References Cited

U.S. PATENT DOCUMENTS

2004/0230040 A1* 11/2004 Cox, III ........................ 530/351

FOREIGN PATENT DOCUMENTS

EP 0 422 697 A1 * 4/1991

* cited by examiner

*Primary Examiner* — Robert Landsman
*Assistant Examiner* — Bruce D Hissong
(74) *Attorney, Agent, or Firm* — Fox Rothschild LLP; Jianming Jimmy Hao

(57) ABSTRACT

The invention relates to variants of consensus interferon protein with improved properties, such as improved anti-viral activity, and use thereof The variants are also easier to renature after denaturant treatment. The invention also relates to the preparation method of the variants consensus interferon.

6 Claims, 5 Drawing Sheets

The consensus interferon sequences

```
1      ATGTGTGATTTACCTCAAACTCATTCTCTTGGTAACCGTCGCGCTCTGATTCTGCTGGCA
1      METCysAspLeuProGlnThrHisSerLeuGlyAsnArgArgAlaLeuIleLeuLeuAla

61     CAGATGCGTCGTATTTCCCCGTTTAGCTGCCTGAAAGACCGTCACGACTTCGGCTTTCCG
21     GlnMETArgArgIleSerProPheSerCysLeuLysAspArgHisAspPheGlyPhePro

121    CAAGAAGAATTCGATGGCAACCAATTCCAGAAAGCTCAGGCAATCTCTGTACTGCACGAA
41     GlnGluGluPheAspGlyAsnGlnPheGlnLysAlaGlnAlaIleSerValLeuHisGlu

181    ATGATCCAACAGACCTTCAACCTGTTTTCCACTAAAGACAGCTCTGCTGCTTGGGACGAA
61     METIleGlnGlnThrPheAsnLeuPheSerThrLysAspSerSerAlaAlaTrpAspGlu

241    AGCTTGCTGGAGAAGTTCTACACCGAGCTGTATCAGCAGCTGAACGACCTGGAAGCATGC
81     SerLeuLeuGluLysPheTyrThrGluLeuTyrGlnGlnLeuAsnAspLeuGluAlaCys

301    GTAATCCAGGAAGTTGGTGTAGAAGAGACTCCGCTGATGAACGTCGACTCTATTCTGGCA
101    ValIleGlnGluValGlyValGluGluThrProLeuMETAsnValAspSerIleLeuAla

361    GTTAAAAAGTACTTCCAGCGTATCACTCTGTACCTGACCGAAAAGAAATATTCTCCGTGC
121    ValLysLysTyrPheGlnArgIleThrLeuTyrLeuThrGluLysLysTyrSerProCys

421    GCTTGGGAAGTAGTTCGCGCTGAAATTATGCGTTCTTTCTCTCTGAGCACTAACCTGCAG
141    AlaTrpGluValValArgAlaGluIleMETArgSerPheSerLeuSerThrAsnLeuGln

481    GAGCGTCTGCGCCGTAAAGAATAA   (SEQ ID NO: 2)
161    GluArgLeuArgArgLysGlu***   (SEQ ID NO: 1)
```

FIG. 1A

A variant of consensus interferon

```
1     ATGTGTGATTTACCTCAAACTCATTCTCTTGGTAACCGTCGCGCTCTGATTCTGCTGGCA
1     METCysAspLeuProGlnThrHisSerLeuGlyAsnArgArgAlaLeuIleLeuLeuAla

61    CAGATGCGTCGTATTTCCCCGTTTAGCTGCCTGAAAGACCGTCACGACTTCGGCTTTCCG
21    GlnMETArgArgIleSerProPheSerCysLeuLysAspArgHisAspPheGlyPhePro

121   CAAGAAGAATTCGATGGCAACCAATTCCAGAAAGCTCAGGCAATCTCTGTACTGCACGAA
41    GlnGluGluPheAspGlyAsnGlnPheGlnLysAlaGlnAlaIleSerValLeuHisGlu

181   ATGATCCAACAGACCTTCAACCTGTTTTCCACTAAAGACAGCTCTGCTGCTTGGGACGAA
61    METIleGlnGlnThrPheAsnLeuPheSerThrLysAspSerSerAlaAlaTrpAspGlu

241   AGCTTGCTGGAGAAGTTCTACACCGAGCTGTATCAGCAGCTGAACGACCTGGAAGCATGC
81    SerLeuLeuGluLysPheTyrThrGluLeuTyrGlnGlnLeuAsnAspLeuGluAlaCys

301   GTAATCCAGGAAGTTGGTGTAGAAGAGACTCCGCTGATGAACGAGGACTCTATTCTGGCA
101   ValIleGlnGluValGlyValGluGluThrProLeuMETAsnGluAspSerIleLeuAla

361   GTTCGCAAGTACTTCCAGCGTATCACTCTGTACCTGACCGAAAAGAAATATTCTCCGTGC
121   ValArgLysTyrPheGlnArgIleThrLeuTyrLeuThrGluLysLysTyrSerProCys

421   GCTTGGGAAGTAGTTCGCGCTGAAATTATGCGTTCTTTCTCTCTGAGCACTAACCTGCAG
141   AlaTrpGluValValArgAlaGluIleMETArgSerPheSerLeuSerThrAsnLeuGln

481   GAGCGTCTGCGCCGTAAAGAATAATAG    (SEQ ID NO:4)
161   GluArgLeuArgArgLysGlu******    (SEQ ID NO:3)
```

FIG. 1B

A variant of consensus interferon

```
1      ATGTGTGATTTACCTCAAACTCATTCTCTTGGTAACCGTCGCGCTCTGATTCTGCTGGCA
1      METCysAspLeuProGlnThrHisSerLeuGlyAsnArgArgAlaLeuIleLeuLeuAla

61     CAGATGCGTCGTATTTCCCCGTTTAGCTGCCTGAAAGACCGTCACGACTTCGGCTTTCCG
21     GlnMETArgArgIleSerProPheSerCysLeuLysAspArgHisAspPheGlyPhePro

121    CAAGAAGAATTCGATGGCAACCAATTCCAGAAAGCTCAGGCAATCTCTGTACTGCACGAA
41     GlnGluGluPheAspGlyAsnGlnPheGlnLysAlaGlnAlaIleSerValLeuHisGlu

181    ATGATCCAACAGACCTTCAACCTGTTTTCCACTAAAGACAGCTCTGCTGCTTGGGACGAA
61     METIleGlnGlnThrPheAsnLeuPheSerThrLysAspSerSerAlaAlaTrpAspGlu

241    AGCTTGCTGGAGAAGTTCTACACCGAGCTGTATCAGCAGCTGAACGACCTGGAAGCATGC
81     SerLeuLeuGluLysPheTyrThrGluLeuTyrGlnGlnLeuAsnAspLeuGluAlaCys

301    GTAATCCAGGAAGTTGGTGTAGAAGAGACTCCGCTGATGAACGAGGACTCTATTCTGGCA
101    ValIleGlnGluValGlyValGluGluThrProLeuMETAsnGluAspSerIleLeuAla

361    GTTCGCAAGTACTTCCAGCGTATCACTCTGTACCTGACCGAAAAGAAATATTCTCCGTGC
121    ValArgLysTyrPheGlnArgIleThrLeuTyrLeuThrGluLysLysTyrSerProCys

421    GCTTGGGAAGTAGTTCGCGCTGAAATTATGCGTTCTTTCTCTCTGTGTACTAACCTGCAG
141    AlaTrpGluValValArgAlaGluIleMETArgSerPheSerLeuCysThrAsnLeuGln

481    GAGCGTCTGCGCCGTAAAGAATAATAG    (SEQ ID NO:6)
161    GluArgLeuArgArgLysGlu******    (SEQ ID NO:5)
```

FIG. 1C

SEQUENCE LISTING

```
<160> NUMBER OF SEQ ID NOS: 8

<210> SEQ ID NO 1
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165


<210> SEQ ID NO 2
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(501)

<400> SEQUENCE: 2

atg tgt gat tta cct caa act cat tct ctt ggt aac cgt cgc gct ctg       48
Met Cys Asp Leu Pro Gln Thr His Ser Leu Gly Asn Arg Arg Ala Leu
1               5                   10                  15

att ctg ctg gca cag atg cgt cgt att tcc ccg ttt agc tgc ctg aaa       96
Ile Leu Leu Ala Gln Met Arg Arg Ile Ser Pro Phe Ser Cys Leu Lys
            20                  25                  30

gac cgt cac gac ttc ggc ttt ccg caa gaa gaa ttc gat ggc aac caa      144
Asp Arg His Asp Phe Gly Phe Pro Gln Glu Glu Phe Asp Gly Asn Gln
        35                  40                  45

ttc cag aaa gct cag gca atc tct gta ctg cac gaa atg atc caa cag      192
Phe Gln Lys Ala Gln Ala Ile Ser Val Leu His Glu Met Ile Gln Gln
    50                  55                  60

acc ttc aac ctg ttt tcc act aaa gac agc tct gct gct tgg gac gaa      240
Thr Phe Asn Leu Phe Ser Thr Lys Asp Ser Ser Ala Ala Trp Asp Glu
```

```
65                  70                  75                  80

agc ttg ctg gag aag ttc tac acc gag ctg tat cag cag ctg aac gac      288
Ser Leu Leu Glu Lys Phe Tyr Thr Glu Leu Tyr Gln Gln Leu Asn Asp
                85                  90                  95

ctg gaa gca tgc gta atc cag gaa gtt ggt gta gaa gag act ccg ctg      336
Leu Glu Ala Cys Val Ile Gln Glu Val Gly Val Glu Glu Thr Pro Leu
            100                 105                 110

atg aac gtc gac tct att ctg gca gtt aaa aag tac ttc cag cgt atc      384
Met Asn Val Asp Ser Ile Leu Ala Val Lys Lys Tyr Phe Gln Arg Ile
        115                 120                 125

act ctg tac ctg acc gaa aag aaa tat tct ccg tgc gct tgg gaa gta      432
Thr Leu Tyr Leu Thr Glu Lys Lys Tyr Ser Pro Cys Ala Trp Glu Val
    130                 135                 140

gtt cgc gct gaa att atg cgt tct ttc tct ctg agc act aac ctg cag      480
Val Arg Ala Glu Ile Met Arg Ser Phe Ser Leu Ser Thr Asn Leu Gln
145                 150                 155                 160

gag cgt ctg cgc cgt aaa gaa taa                                      504
Glu Arg Leu Arg Arg Lys Glu
                165


<210> SEQ ID NO 3
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Glu Asp Ser Ile Leu Ala Val Arg Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165


<210> SEQ ID NO 4
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

```
<222> LOCATION: (1)..(501)

<400> SEQUENCE: 4

atg tgt gat tta cct caa act cat tct ctt ggt aac cgt cgc gct ctg       48
Met Cys Asp Leu Pro Gln Thr His Ser Leu Gly Asn Arg Arg Ala Leu
1               5                   10                  15

att ctg ctg gca cag atg cgt cgt att tcc ccg ttt agc tgc ctg aaa       96
Ile Leu Leu Ala Gln Met Arg Arg Ile Ser Pro Phe Ser Cys Leu Lys
            20                  25                  30

gac cgt cac gac ttc ggc ttt ccg caa gaa gaa ttc gat ggc aac caa      144
Asp Arg His Asp Phe Gly Phe Pro Gln Glu Glu Phe Asp Gly Asn Gln
        35                  40                  45

ttc cag aaa gct cag gca atc tct gta ctg cac gaa atg atc caa cag      192
Phe Gln Lys Ala Gln Ala Ile Ser Val Leu His Glu Met Ile Gln Gln
    50                  55                  60

acc ttc aac ctg ttt tcc act aaa gac agc tct gct gct tgg gac gaa      240
Thr Phe Asn Leu Phe Ser Thr Lys Asp Ser Ser Ala Ala Trp Asp Glu
65                  70                  75                  80

agc ttg ctg gag aag ttc tac acc gag ctg tat cag cag ctg aac gac      288
Ser Leu Leu Glu Lys Phe Tyr Thr Glu Leu Tyr Gln Gln Leu Asn Asp
                85                  90                  95

ctg gaa gca tgc gta atc cag gaa gtt ggt gta gaa gag act ccg ctg      336
Leu Glu Ala Cys Val Ile Gln Glu Val Gly Val Glu Glu Thr Pro Leu
            100                 105                 110

atg aac gag gac tct att ctg gca gtt cgc aag tac ttc cag cgt atc      384
Met Asn Glu Asp Ser Ile Leu Ala Val Arg Lys Tyr Phe Gln Arg Ile
        115                 120                 125

act ctg tac ctg acc gaa aag aaa tat tct ccg tgc gct tgg gaa gta      432
Thr Leu Tyr Leu Thr Glu Lys Lys Tyr Ser Pro Cys Ala Trp Glu Val
    130                 135                 140

gtt cgc gct gaa att atg cgt tct ttc tct ctg agc act aac ctg cag      480
Val Arg Ala Glu Ile Met Arg Ser Phe Ser Leu Ser Thr Asn Leu Gln
145                 150                 155                 160

gag cgt ctg cgc cgt aaa gaa taatag                                   507
Glu Arg Leu Arg Arg Lys Glu
                165


<210> SEQ ID NO 5
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110
```

```
Met Asn Glu Asp Ser Ile Leu Ala Val Arg Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Cys Thr Asn Leu Gln
145                 150                 155                 160

Glu Arg Leu Arg Arg Lys Glu
                165


<210> SEQ ID NO 6
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(501)

<400> SEQUENCE: 6

atg tgt gat tta cct caa act cat tct ctt ggt aac cgt cgc gct ctg       48
Met Cys Asp Leu Pro Gln Thr His Ser Leu Gly Asn Arg Arg Ala Leu
1               5                   10                  15

att ctg ctg gca cag atg cgt cgt att tcc ccg ttt agc tgc ctg aaa       96
Ile Leu Leu Ala Gln Met Arg Arg Ile Ser Pro Phe Ser Cys Leu Lys
            20                  25                  30

gac cgt cac gac ttc ggc ttt ccg caa gaa gaa ttc gat ggc aac caa      144
Asp Arg His Asp Phe Gly Phe Pro Gln Glu Glu Phe Asp Gly Asn Gln
        35                  40                  45

ttc cag aaa gct cag gca atc tct gta ctg cac gaa atg atc caa cag      192
Phe Gln Lys Ala Gln Ala Ile Ser Val Leu His Glu Met Ile Gln Gln
    50                  55                  60

acc ttc aac ctg ttt tcc act aaa gac agc tct gct gct tgg gac gaa      240
Thr Phe Asn Leu Phe Ser Thr Lys Asp Ser Ser Ala Ala Trp Asp Glu
65                  70                  75                  80

agc ttg ctg gag aag ttc tac acc gag ctg tat cag cag ctg aac gac      288
Ser Leu Leu Glu Lys Phe Tyr Thr Glu Leu Tyr Gln Gln Leu Asn Asp
                85                  90                  95

ctg gaa gca tgc gta atc cag gaa gtt ggt gta gaa gag act ccg ctg      336
Leu Glu Ala Cys Val Ile Gln Glu Val Gly Val Glu Glu Thr Pro Leu
            100                 105                 110

atg aac gag gac tct att ctg gca gtt cgc aag tac ttc cag cgt atc      384
Met Asn Glu Asp Ser Ile Leu Ala Val Arg Lys Tyr Phe Gln Arg Ile
        115                 120                 125

act ctg tac ctg acc gaa aag aaa tat tct ccg tgc gct tgg gaa gta      432
Thr Leu Tyr Leu Thr Glu Lys Lys Tyr Ser Pro Cys Ala Trp Glu Val
    130                 135                 140

gtt cgc gct gaa att atg cgt tct ttc tct ctg tgt act aac ctg cag      480
Val Arg Ala Glu Ile Met Arg Ser Phe Ser Leu Cys Thr Asn Leu Gln
145                 150                 155                 160

gag cgt ctg cgc cgt aaa gaa taatag                                   507
Glu Arg Leu Arg Arg Lys Glu
                165


<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

```
atatagctta agctagaaac catgagggta ataaataatg tgtgatttac ctcaa         55


<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

atatagtcta gactattatt ctttacggc                                      29
```

CONSENSUS INTERFERON VARIANT AND METHODS OF SUPPRESSING VIRAL ACTIVITY

This application is a continuation application of U.S. Ser. No. 12/446,519, filed Jul. 6, 2010, which is a national stage entry from PCT/CN09/70607, filed Mar. 2, 2009, which claims priority to CN200810101309.4, filed on Mar. 4, 2008, which are all incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 1, 2012, is named 40391-701-301Seqlist.txt and is 13,694 bytes in size.

FIELD OF THE INVENTION

The invention relates to variants of consensus interferon with improved properties, and to methods of making and to methods and compositions utilizing these variants.

BACKGROUND OF THE INVENTION

Interferons (IFNs) are a subclass of cytokines that exhibit both antiviral and antiproliferative activity, and is widely used in clinical treatment of hepatitis, inflammation and cancer. On the basis of biochemical and immunological properties, the naturally-occurring human interferons are grouped into three classes: interferon α (leukocyte), interferon β (fibroblast) and interferon γ (immune).

U.S. Pat. Nos. 4,695,623, 4,897,471 and 5,541,293 disclose human interferon polypeptides having amino acid sequences which include common or predominant amino acids found at each position among naturally-occurring alpha interferon subtype polypeptides and are referred to as consensus interferons (IFN-con). The IFN-con amino acid sequences disclosed are designated IFN-$con_1$, IFN-$con_2$, and $IFNcon_3$. The preparation of manufactured genes encoding IFN-con and the expression of said genes in *E. coli* are also disclosed. In vitro studies comparing the relative antiviral, antiproliferative, and natural killer cell activities of recombinant IFN-con with either leukocyte or other recombinant type-one interferons demonstrate that IFN-con displays significantly higher activity when compared on a mass basis; Ozes et al., J Interferon Research, 12:55-59, 1992. U.S. FDA approved consensus Interferon developed by Amgen in 1997 (INFERGEN™)

There are two trends in developing interferon product: to develop highly-active interferon and long-acting interferon. Consensus interferon INFERGEN™ is representative of highly-active interferon. The activity of consensus interferon obtained by comparing more than ten kinds of natural interferon and designing artificial sequence is greatly higher than that of natural interferon (5-10 times). "Pegasys" and "PEG-Intron" developed by Roche Company and Schering-Plough Corporation respectively are long-acting interferon and their annual sales exceed $1 billions, thus they are "blockbuster" biological-technical drugs. The two drugs extend the half-life of interferon by PEG-modification, while the activity of product is largely dependent on the initial activity of the modified interferon. Therefore, the development of highly-active interferon is an important factor for further optimizing the efficacy of medicament.

INFERGEN™ is produced with *Escherichia coli* system, followed by a in vitro folding process (the inclusion body is processed by denaturant, and then is re-natured to make the active structure of denatured protein wholly resumed). However, studies revealed that although the activity of consensus interferon is significantly increased, the change of sequence hampers the folding in vitro.

Thus there is a need for improvement of consensus interferon.

SUMMARY OF THE INVENTION

The present invention provides a variant consensus interferon protein (SEQ ID NO: 3) of a parent consensus interferon protein (SEQ ID NO:1). The variant has two modifications that are V115E and L122R. The present invention also provides a variant consensus interferon protein (SEQ ID NO: 5) of a parent consensus interferon protein (SEQ ID NO:1). The variant has three modifications that are V115E, L122R, and S156C.

The present invention further provides a variant consensus interferon protein having the amino acid sequence of SEQ ID NO: 5, and the variant protein comprises a PEG moiety at position 156. In some embodiments, the PEG moiety is (PEG)n. In some embodiments, the PEG moiety is a PEG derivative.

The present invention also provides DNA encoding the variant consensus interferon, expression vectors comprise such DNA, host cells that express variant consensus interferon, as well as methods to manufacture variant consensus interferon.

The present invention also provides a pharmaceutical composition comprising the variant consensus interferon protein provided herein and a pharmaceutically acceptable excipient.

BRIEF DESCRIPTION OF THE DRAWINGS

FIGS. 1A-1C depict the consensus interferon and variants thereof

DETAILED DESCRIPTION OF THE INVENTION

Figure 2:
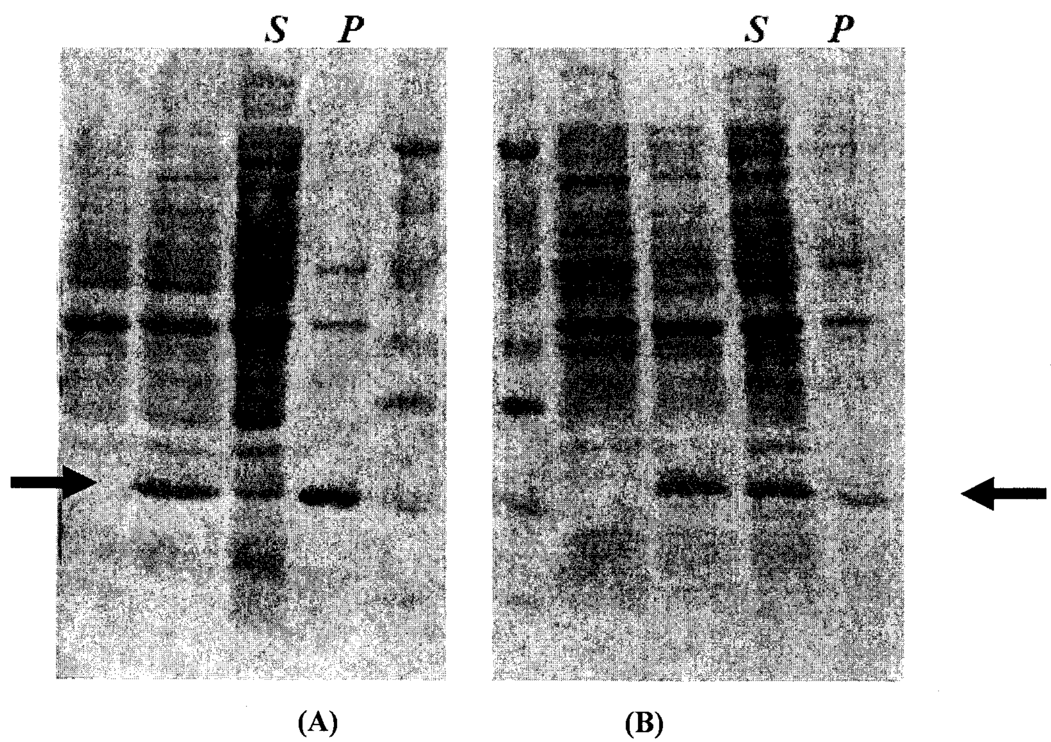
FIG. 2 depicts the SDS-PAGE analysis of parent consensus interferon (A) and variant interferon ((V115E/L122R/S156C)) (B). The lanes from left to right in sequence are of whole cell lysate before induction, whole cell lysate after induction, supernatant portion S and precipitation portion P after ultrasonic disruption and centrifugation. The target band is marked by an arrow. The fifth lane in panel (A) and the first lane in panel (B) are standard molecular weight markers.

The present invention provides variants of consensus interferon (some time referred to as a "variant IFN protein") with improved refolding properties and/or biological activities.

I. Variants of Consensus Interferon

Through an optimizing process, natural interferon can fold into active structure in vitro. However, generally, there is always a portion of consensus interferon that has low or no biological activities due to improper folding. To meet the requirement of homogeneity generally required in pharmaceutical products, a costly complex separation process is often required to separate the misfolded, low-activity interferon from the properly folded interferon. The present invention provided variant interferons based on structural biology studies that have improved refolding properties, and which also resume an active structure more easily after treatment of denaturant, as compared to the parent consensus interferon.

In one aspect, the present invention provides a variant consensus interferon protein (V115E/L122R) (SEQ ID NO: 3) of a parent consensus interferon protein (SEQ ID NO:1). The variant has two modifications: V115E and L122R, and is sometimes referred as "the double variant."

In another aspect, the present invention provides a variant consensus interferon protein (V115E/L122R/S156C) (SEQ ID NO: 5) of a parent consensus interferon protein (SEQ ID NO:1). The variant has three modifications: V115E, L122R, and S156C, and is sometimes referred as "the triple variant".

In another aspect, the present invention provides the trip mutant further comprising a PEG moiety, which is preferably attached at the S156C position.

II. Expression Vectors and DNA Encoding Variant IFN Proteins

In another aspect, the present invention provides a DNA encoding the consensus interferon variant protein that has the amino acid sequences of SEQ ID NO:3 or SEQ ID NO:5. In some embodiments, the DNA has the nucleotide sequences of SEQ ID NO:4 or SEQ ID NO:6. In one embodiment, nucleic acids encoding IFN variants are prepared by total gene synthesis, or by site-directed mutagenesis of a nucleic acid encoding wild type or variant IFN protein. Methods including template-directed ligation, recursive PCR, cassette mutagenesis, site-directed mutagenesis or other techniques that are well known in the art may be utilized (see for example Strizhov et. al. PNAS 93:15012-15017 (1996), Prodromou and Perl, Prot. Eng. 5: 827-829 (1992), Jayaraman and Puccini.

In one aspect, the present invention provides an expression vector comprising the DNA that encodes the consensus interferon variant protein that has the amino acid sequences of SEQ ID NO:3 or SEQ ID NO:5. In some embodiments, the expression vector comprises the DNA has the nucleotide sequences of SEQ ID NO:4 or SEQ ID NO:6.

In some embodiments, a variant IFN nucleic acid encodes a variant IFN protein. As will be appreciated by those in the art, due to the degeneracy of the genetic code, an extremely large number of nucleic acids may be made, all of which encode the variant IFN proteins of the present invention. Thus, having identified a particular amino acid sequence, those skilled in the art could make any number of different nucleic acids, by simply modifying the sequence of one or more codons in a way which does not change the amino acid sequence of the variant IFN.

In one embodiment, the nucleic acid homology is determined through hybridization studies. Thus, for example, nucleic acids which hybridize under high stringency to the nucleic acid sequences shown in FIG. 1 (SEQ ID NO:4 and SEQ ID NO:6) or their complement is considered a variant IFN gene. High stringency conditions are known in the art; see for example Maniatis, et al., Molecular Cloning: A Laboratory Manual, 2d Edition (1989), and Short Protocols in Molecular Biology, ed. Ausubel, et al., both of which are hereby incorporated by reference. An example of such conditions includes hybridization at about 42° C. in about 6×SSC with 50% formamide and washing conditions of about 65° C. in about 0.2×SSC, 0.1×SDS.

In another embodiment, less stringent hybridization conditions are used; for example, moderate or low stringency conditions may be used, as are known in the art; see Maniatis and Ausubel, supra. An example of such conditions includes hybridization at about 50 to 55° C. in 5×SSPE and washing conditions of about 50° C. in about 5×SSPE.

The variant IFN proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated variant IFN nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant IFN protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may have addition of an epitope tag or amino acid substitutions, insertions and deletions, as discussed herein.

In one embodiment, an expression vector that comprises the components described below and a gene encoding a variant IFN protein is prepared. Numerous types of appropriate expression vectors and suitable regulatory sequences for a variety of host cells are known in the art for a variety of host cells. The expression vectors may contain transcriptional and translational regulatory sequences including but not limited to promoter sequences, ribosomal binding sites, transcriptional start and stop sequences, translational start and stop sequences, transcription terminator signals, polyadenylation signals, and enhancer or activator sequences. In one embodiment, the regulatory sequences include a promoter and transcriptional start and stop sequences. In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences, which flank the expression construct. The integrating vector may be directed to a specific locus in the host cell by selecting the appropriate homologous sequence for inclusion in the vector. Constructs for integrating vectors are well known in the art. In addition, in a preferred embodiment, the expression vector contains a selectable marker gene to allow the selection of transformed host cells. Selection genes are well known in the art and will vary with the host cell used. The expression vectors may be either self-replicating extrachromosomal vectors or vectors which integrate into a host genome. The expression vector may include a secretory leader sequence or signal peptide sequence that provides for secretion of the variant IFN protein from the host cell. Suitable secretory leader sequences that lead to the secretion of a protein are known in the art. The signal sequence typically encodes a signal peptide comprised of hydrophobic amino acids, which direct the secretion of the protein from the cell, as is well known in the art. The protein is either secreted into the growth media or, for prokaryotes, into the periplasmic space, located between the inner and outer membrane of the cell. For expression in bacteria, usually bacterial secretory leader sequences, operably linked to a variant IFN encoding nucleic acid, are usually preferred.

In one aspect, the present provide host cells comprising the DNA that encodes the consensus interferon variant protein that having the amino acid sequences of SEQ ID NO:3 or SEQ ID NO:5. In some embodiments, the host cell comprises the DNA has the nucleotide sequences of SEQ ID NO:2 or SEQ ID NO:4.

III. Methods of Making Variant IFN Proteins

In one aspect, the present invention provides a method of manufacturing a consensus interferon, the method comprising the steps of: growing the host cell provided herein under a condition that the variant IFN can be expressed, harvesting the host cell, and purifying the interferon consensus variants.

Transfection/Transformation. The variant IFN nucleic acids are introduced into the cells either alone or in combination with an expression vector in a manner suitable for subsequent expression of the nucleic acid. The method of introduction is largely dictated by the targeted cell type, as discussed below. Exemplary methods include $CaPO_4$ precipitation, liposome fusion, Lipofectin®, electroporation, viral infection, dextran-mediated transfection, polybrene mediated transfection, protoplast fusion, direct microinjection, etc. The variant IFN nucleic acids may stably integrate into the genome of the host cell or may exist either transiently or stably in the cytoplasm.

Appropriate host cells for the expression of IFN variants. Appropriate host cells for the expression of IFN variants include yeast, bacteria, archaebacteria, fungi, and insect and animal cells, including mammalian cells. Of particular interest are bacteria such as *E. coli* and *Bacillus subtilis*, fungi such as *Saccharomyces cerevisiae, Pichia pastoris*, and *Neurospora*, insects such as *Drosophila melangaster* and insect cell lines such as SF9, mammalian cell lines including 293, CHO, COS, Jurkat, NIH3T3, etc (see the ATCC cell line catalog, hereby expressly incorporated by reference).

Interferon variants can also be produced in more complex organisms, including but not limited to plants (such as corn, tobacco, and algae) and animals (such as chickens, goats, cows); see for example Dove, Nature Biotechnol. 20: 777-779 (2002).

In one embodiment, the cells may be additionally genetically engineered, that is, contain exogenous nucleic acid other than the expression vector comprising the variant IFN nucleic acid.

Expression methods. The variant IFN proteins of the present invention are produced by culturing a host cell transformed with an expression vector containing nucleic acid encoding a variant IFN protein, under the appropriate conditions to induce or cause expression of the variant IFN protein. The conditions appropriate for variant IFN protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Purification. In one embodiment, the IFN variants are purified or isolated after expression. Standard purification methods include electrophoretic, molecular, immunological and chromatographic techniques, including ion exchange, hydrophobic, affinity, and reverse-phase HPLC chromatography, and chromatofocusing. For example, a IFN variant may be purified using a standard anti-recombinant protein antibody column. Ultrafiltration and diafiltration techniques, in conjunction with protein concentration, are also useful. For general guidance in suitable purification techniques, see Scopes, R., Protein Purification, Springer-Verlag, NY, 3dr ed. (1994). The degree of purification necessary will vary depending on the desired use, and in some instances no purification will be necessary.

IV. Posttranslational Modification and Derivitization

Once made, the variant IFN proteins may be covalently modified. Covalent and non-covalent modifications of the protein are thus included within the scope of the present invention. Such modifications may be introduced into a variant IFN polypeptide by reacting targeted amino acid residues of the polypeptide with an organic derivatizing agent that is capable of reacting with selected side chains or terminal residues. Optimal sites for modification can be chosen using a variety of criteria, including but not limited to, visual inspection, structural analysis, sequence analysis and molecular simulation.

In one embodiment, the variant IFN proteins of the invention are labeled with at least one element, isotope or chemical compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Labels include but are not limited to biotin, tag (e.g. FLAG, Myc) and fluorescent labels (e.g. fluorescein).

In general, the amino acid modification provided herein improves the refolding and recovery rate in comparison to the consensus interferon protein without the modification.

Preferably, the variant consensus interferon protein also improves the antiviral activities in comparison to that of the parent consensus interferon protein.

In another aspect, the present invention provides a variant consensus interferon protein having the amino acid sequence of SEQ ID NO: 5, and the variant protein comprises a PEG moiety at position 156. As used herein, the term "PEG moiety" is intended to include, but is not limited to, linear and branched PEG, methoxy PEG, hydrolytically or enzymatically degradable PEG, pendant PEG, dendrimer PEG, copolymers of PEG and one or more polyols, and copolymers of PEG and PLGA (poly(lactic/glycolic acid)). In some embodiments, the PEG moiety is (PEG)n, including the terminal hydrogen as appropriate. That is, if a three unit PEG polymer is used, the moiety is $(CH_2CH_2O)_3$—H . In some embodiments, the PEG moiety is a PEG derivative. As noted herein, for ease of discussion the term "PEG" is used below, but is meant to include the scope of "polymeric moiety" as defined below.

The effect of polymeric moiety attachment to a protein depends both on the site(s) of attachment and the size(s) of the polymers. The highly flexible attached PEG moiety experiences a wide range of conformations that change depending on the location of attachment and the number of monomer units in the moiety (i.e. the PEG size). The range of conformations that an attached PEG can fold depends directly on its size and its molecular surroundings. Conformations that overlap with atoms in the protein are generally prohibited due to steric clash. If the molecular surroundings change, as is the case when a PEGylated protein binds to another protein, the range of allowed conformations for the attached PEG can change dramatically. The fundamental tenets of statistical mechanics predict that this reduction of PEG conformations, known thermodynamically as a reduction of entropy, will lead to a reduced interaction affinity between the PEGylated protein and its binding partner.

As used in this invention, the term "polymer" and "polymeric moiety" or its grammatical equivalents means any non-monomeric moiety that is attachable to a protein, is at least partially soluble and has the appropriate flexibility to achieve a desired function. The polymer can be homopolymeric or heteropolymeric. In a preferred embodiment of the invention, polymer moieties may include but are not limited to alcohol such as glycols moieties and carbohydrate moieties. A preferred range of molecular weight is about 1000 Daltons to about 100,000 Daltons. The polymer may be unbranched, branched, or labile, including both internal lability, e.g. cleavage upon introduction into a patient, as well as attachment lability, wherein the linkage between the protein and the polymer is reversible. The polymer may have organic or inorganic components or moieties. In some embodiments, the polymer is pharmaceutically acceptable and may be attached to therapeutic proteins. A preferred example of a suitable polymer is polyethylene glycol (PEG) ($(CH_2CH_2O)_n$—H) and its derivatives. For ease of discussion, the term "PEG" will be used, but is meant to include the scope of the term "polymer" as defined above. Examples of suitable polymers include, but are not limited to, example Roberts, M. J. et al. (2002) "Chemistry for peptide and protein PEGylation" Adv. Drug Deliv. Rev. 54, 459-476 and Kinstler, O. et al. (2002) "Mono-N-terminal poly(ethylene glycol)-protein conjugates" Adv. Drug Deliv. Rev. 54; U.S. Ser. No. 60/360,722; U.S. Pat. No. 5,795,569; U.S. Pat. No. 5,766,581; EP 01064951; U.S. Pat. No. 6,340,742; WO 00176640; WO 002017; EP0822199A2; WO 0249673A2; U.S. Pat. No. 4,002,531; U.S. Pat. No. 5,183,550; U.S. Pat. No. 5,985,263; U.S. Pat. No. 5,990,237; U.S. Pat. No. 6,461,802; U.S. Pat. No. 6,495,659; U.S. Pat. No. 6,448,369; U.S. Pat. No. 6,437,025; U.S. Pat. No. 5,900,461; U.S. Pat. No. 6,413,507; U.S. Pat. No. 5,446,090; U.S. Pat. No. 5,672,662; U.S. Pat. No. 6,214,966; U.S. Pat. No. 6,258,351; U.S. Pat. No. 5,932,462; U.S. Pat. No. 5,919,455; U.S. Pat. No. 6,113,906; U.S. Pat. No. 5,985,236; WO 9428024A1; U.S. Pat. No. 6,340,742; U.S. Pat. No. 6,420,339; and WO 0187925A2, all hereby incorporated by reference. PEG derivatives can include heteroatoms and substitution groups for hydrogen atoms, and polymers can include mixtures of "normal" PEG with derivatized PEGs.

The PEG-IFN conjugates of the present invention can be prepared by any of the methods known in the art. U.S. Pat. No. 6,638,500, herein is incorporated by reference in its entirety. According to an embodiment of the invention, variant IFN- is reacted with the PEGylating agent in a suitable solvent and the desired conjugate is isolated and purified, for example, by applying one or more chromatographic methods.

V. Assaying the Activity of the Variants

In some embodiments, the wild-type and variant proteins are analyzed for biological activities by suitable methods known in the art. Such assays include but are not limited to activation of interferon-responsive genes, receptor binding assays, antiviral activity assays, cytopathic effect inhibition assays, (Familletti et. al., Meth. Enzymol. 78:387-394), antiproliferative assays, (Aebersold and Sample, Meth. Enzymol. 119:579-582), immunomodulatory assays (U.S. Pat. Nos. 4,914,033; 4,753,795), and assays that monitor the induction of MHC molecules (for example, Hokland et al, Meth. Enzymol. 119:688-693), as described in Meager, J. Immunol. Meth., 261:21-36 (2002).

In on embodiment, wild type and variant proteins will be analyzed for their ability to activate interferon-sensitive signal transduction pathways. One example is the interferon-stimulated response element (ISRE) assay, described below and in the Examples. Cells which constitutively express the type I interferon receptor (for example Hela cells, 293T cells) are transiently transfected with an ISRE-luciferase vector. After transfection, the cells are treated with an interferon variant. In a preferred embodiment, a number of protein concentrations, for example from 0.0001-10 ng/mL, are tested to generate a dose-response curve. In an alternate embodiment, two or more concentrations are tested. If the variant binds and activates its receptor, the resulting signal transduction cascade induces luciferase expression. Luminseescence can be measured in a number of ways, for example by using a TopCount™ or Fusion™ microplate reader.

In one embodiment, variant proteins are be analyzed for their ability to bind to the type I interferon receptor (IFNAR), and compared to the wild type IFNS or parent consensus IFN. Suitable binding assays include, but are not limited to, BIAcore assays (Pearce et al., Biochemistry 38:81-89 (1999)) and AlphaScreen™ assays (commercially available from PerkinElmer) (Bosse R., Illy C., and Chelsky D (2002). Principles of AlphaScreen™ PerkinElmer Literature Application Note Ref# s4069. AlphaScreen™ is a bead-based non-radioactive luminescent proximity assay where the donor beads are excited by a laser at 680 nm to release singlet oxygen. The singlet oxygen diffuses and reacts with the thioxene derivative on the surface of acceptor beads leading to fluorescence emission at ~600 nm. The fluorescence emission occurs only when the donor and acceptor beads are brought into close proximity by molecular interactions occurring when each is linked to ligand and receptor respectively. This ligand-receptor interaction can be competed away using receptor-binding variants while non-binding variants will not compete.

In an alternate embodiment, variant proteins are be analyzed for their efficacy in treating an animal model of disease, such as the mouse or rat EAE model for multiple sclerosis, and compared to the wild type IFNS or parent consensus IFN.

In an alternate embodiment, parent consensus interferon and variant proteins are analyzed for their antiviral activity, and compared to the wild type IFNS or parent consensus IFN.

Antiproliferative activity: In an alternate preferred embodiment, wild type and variant proteins will be analyzed for their efficacy in treating an animal model of disease, such as the mouse or rat EAE model for multiple sclerosis, and compared to the wild type IFNS or parent consensus IFN.

VI. Method of Using the IFN Variants

Administration and Treatment using IFN variants. Once made, the variant IFN proteins and nucleic acids of the invention find use in a number of applications. In some embodiments, a variant IFN protein or nucleic acid is administered to a patient to treat an IFN related disorder.

The administration of the variant IFN proteins of the present invention, preferably in the form of a sterile aqueous solution, may be done in a variety of ways, including, but not limited to, orally, parenterally, subcutaneously, intravenously, intranasally, transdermally, intraperitoneally, intramuscularly, intrapulmonary, vaginally, rectally, intranasally or intraocularly. In some instances, the variant IFN protein may be directly applied as a solution or spray. Depending upon the manner of introduction, the pharmaceutical composition may be formulated in a variety of ways.

In one aspect, the present invention provides a pharmaceutical composition comprising the variant consensus interferon protein provided herein and a pharmaceutically accept excipient or carrier.

"Pharmaceutically acceptable carrier" or grammatical equivalents includes pharmaceutically acceptable carriers, excipients or stabilizers (Remington's Pharmaceutical Sciences 16th edition, Osol, A. Ed.,1980), in the form of lyophilized formulations, aqueous solutions, etc. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the compositions of the present invention is in a water-soluble form, such as being present as pharmaceutically acceptable salts, which is meant to include both acid and base addition salts. Acceptable carriers include, but are not limited to pharmaceutically acceptable acid and base salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions of the present invention comprise a variant IFN protein in a form suitable for administration to a patient. In the preferred embodiment, the pharmaceutical compositions are in a water-soluble form, such as being present as pharmaceutically acceptable salts, which is meant to include both acid and base addition salts.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations, and discussed above.

In a further embodiment, the variant IFN proteins are added in a micellular formulation; see U.S. Pat. No. 5,833,948, hereby expressly incorporated by reference in its entirety.

Combinations of pharmaceutical compositions may be administered. Moreover, the compositions may be administered in combination with other therapeutics.

In an embodiment, the nucleic acid encoding the variant IFN proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. The oligonucleotides canmay be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [(Dzau et al., Trends in Biotechnology 11:205-210 (1993))]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990). For review of gene marking and gene therapy protocols see Anderson et al., Science 256:808-813 (1992).

In one aspect, the present invention provides a method of suppressing viral activity in a subject (patient), the method comprising administering an animal or human subject with an therapeutically effective dose of the variant consensus interferon protein provided herein. By "suppressing viral activity" herein is meant the reduction of virus activity. This is measured by methods known in the art, such as viral titer. The suppression of viral activity is preferably by more than 10%, by more than 20%, 30%, 40%, and preferably more than 50%, 60%, 70%, 80% and 90%, or total elimination of viral activity in the subject.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

By "therapeutically effective dose" herein is meant a dose that produces the effects for which it is administered. The exact dose will depend on the purpose of the treatment, and will be ascertainable by one skilled in the art using known techniques. The dosage can be between 10 μg and 1 mg daily for an average body weight of 75 kg, and the preferable daily dose is between 20 μg and 200 μg. In a preferred embodiment, dosages of about 5 μg/kg are used, administered either intravenously or subcutaneously. As is known in the art, adjustments for variant IFN protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

By "treatment" herein is meant to include therapeutic treatment, as well as prophylactic, or suppressive measures for the disease or disorder. Thus, for example, successful administration of a variant IFN protein prior to onset of the disease may result in treatment of the disease. As another example, successful administration of a variant IFN protein after clinical manifestation of the disease to combat the symptoms of the disease comprises "treatment" of the disease. "Treatment" also encompasses administration of a variant IFN protein after the appearance of the disease in order to ameliorate or eradicate the disease. Successful administration of an agent after onset and after clinical symptoms have developed, with possible abatement of clinical symptoms and perhaps amelioration of the disease, further comprises "treatment" of the disease.

While the foregoing invention has been described above, it will be clear to one skilled in the art that various changes and additional embodiments made be made without departing from the scope of the invention. All publications, patents, patent applications (provisional, utility and PCT) or other documents cited herein are incorporated by references in their entirety.

EXAMPLES

Example 1

Obtaining the Sequence of Nucleic Acid of "INFERGEN™"

Based on the amine acid sequence of INFERGEN™ and taking into consideration the genetic code preference in *Escherichia coli* and the convenience in cloning and identification, the present invention provides the DNA sequence of consensus interferon (SEQ ID NO:2) as shown in FIG. 1. The corresponding amino acid sequence (SEQ ID NO:1) is also shown in FIG. 1

According to the DNA sequence provided above, two groups of oligonucleotide fragment were synthesized. There were twelve oligonucleotides in each group, with each oligonucleotide are about 40 mer. The oligonucleotide fragments were overlapped. The two groups were annealed at room temperature separately, and T4 DNA ligase was used to form two double-strand DNA segments. The terminals of the two DNA segments have Hind III ends. After purified by electrophoresis, the two segments of DNA were mixed in equal amount to form an single double-strand DNA using ligase. This single DNA segment was further amplified with PCR using upstream primer ATATAGCTTAAG CTAGAAACCATGAGGGTAATAAATAATG TGTGATTTACCTCAA (SEQ ID NO: 7) and downstream primer ATATAGTCTAGACTAT TATTCTTTACGGC (SEQ ID NO:8). The Afl II restriction sites (CTTAAG) and ribosome binding sequence (the underscored portion of the primer) were introduced to the 5' end, and the Xba I restriction sites (TCTAGA) were introduced to the 3' end. The product of PCR was subjected to Afl II and Xba I double restriction enzyme digest and cloned to the expression vector pTac-CI. The expression carrier pTac-CI was transfected into the *E. coli* BL-21. The transfected *E. coli* was deposited in General Microbiological Culture Collection Center, China Committee for Culture Collection (Datun Road, Chaoyang District, Beijing, Institute of Microbiology, Chinese Academy of Sciences, Post code: 100101). Deposition code: CGMCC 2379.

Example 2

New Type of Interferon Obtained by the Sequence-Engineering of Amine Acids.

Through extensive sequence-engineering of amino acids and screening trials, it was found that: (1) the activity of a variant that obtained by changing Val in site 115 to Glu, and Lys in site 122 to Arg (SEQ ID NO: 3) was improved in comparison to the consensus interferon INFERGEN™; (2) the folding property of variant obtained by further changing Ser in site 156 to Cys (SEQ ID NO: 5) was also significantly improved.

The *E. coli* transfected expressing the above two variants were deposited in General Microbiological Culture Collection Center, China Committee for Culture Collection (Datun Road, Chaoyang District, Beijing, Institute of Microbiology, Chinese Academy of Sciences, Post code: 100101). Deposition code: CGMCC 0978 and CGMCC 2267.

The conIFN plasmid-containing *E. coli* BL21 (DE3) was cultured overnight, and then was seeded into 2 ml LB culture medium containing 100 mg/L of ampicillin, grew at 37° C. for about 2 hours (OD=0.6-0.8). IPTG was added to the culture medium to the final concentration of 0.5 mmol/L. The bacteria was induced by IPTG for 4 hours and then collected by 4000 rpm centrifugation. The collected bacteria was subjected to ultrasonic disruption, followed with centrifuged at 12,000 rpm to collect the supernatant portion and precipitation portion separately, and analyzed with SDS-PAGE. The density of stacking gel was 4%, and the density of separation gel was 12%. The gel was stained for 1 hour with Commassie Brilliant Blue, followed by destaining with methanol-glacial acetic acid. The stained gel was recorded by scan-imaging device Bio-Rad. FIGS. 2A and 2B show the expressions of interferon before and after sequence-engineering respectively, the lanes from left to right in sequence are whole cell lysate before induction, whole cell lysate after induction, supernatant portion S and precipitation portion P after ultrasonic disruption and centrifugation. The target band is marked by an arrow. The quantity and form of expression was primarily estimated according to the band of electrophoresis. The result revealed that the quantity of expression of interferon did not change after sequence-engineering. However, the solubility of interferon changed remarkably. The interferon was in the form of inclusion body existed in the precipitation portion before was mostly shifted to the supernatant. It also initially suggested that the folding-kinetics of interferon was accelerated in molecule level after sequence-engineering. This is because the formation of due to higher expression rate of recombination protein than the folding rate of recombination protein in vivo in the prokaryotic expression system, such that a great deal of protein that do not fold into correct three-dimensional structure congregate, and form insoluble precipitation.

Example 2

Study on Folding Nature

The inclusion body of parent consensus IFN and variant interferon were washed by three kinds of eluant to obtain highly pure inclusion body for the analysis of folding properties. The inclusion body after washing was dissolved by denaturant (1g inclusion body was dissolved in 10m1 denaturant), and placed at room temperature for 12 hours, then the gained denatured protein was centrifuged at 15000rpm for 20 minutes.

The formulation of specific solution was as follows:

Eluant 1: 20 mM Tris, 1 mM EDTA, 1% Triton X-100, pH8.5

Eluant 2: 20 mM Tris, 1 mM EDTA, 1M NaCl, pH8.5

Eluant 3: 20 mM Tris, 1 mM EDTA, 2M urea, pH8.5

Denaturant: 6M guanidinium hydrochloride, 50 mM Tris, 1 mM EDTA, 1% β-mercaptoethanol, pH8.5.

Figure 3:
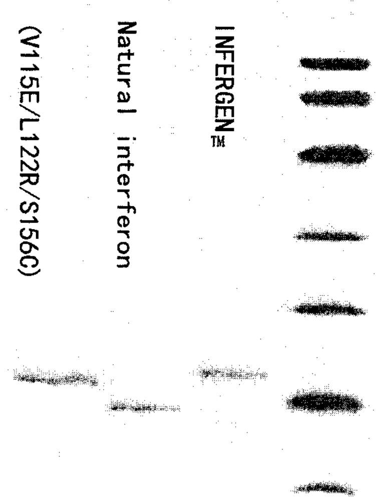
FIG. 3 depicts SDS-PAGE analysis three types of interferon. The lanes from left to right in sequence are: the triple variant consensus interferon (V115E/L122R/S156C), IFN-α2b and "INFERGEN™". The fourth lane is standard molecular weight markers.
Figure 4:
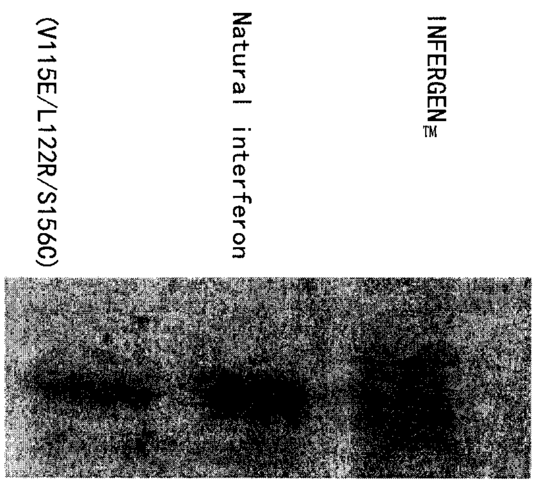
FIG. 4 shows the non-reduced SDS-PAGE electrophoresis result of three kinds of interferon, the lanes from left to right in sequence are: the triple variant consensus interferon (V115E/L122R/S156C), IFN-α2b and "INFERGEN™".

The inclusion body was purified in some extent after the above washing step. The renaturation trial was carried out in order to investigate the folding nature of interferon before and after sequence-engineering. The natural IFN-α2b was used as control. It has been reported that in specific renaturation condition, the natural interferon could be revived to have proper three dimensional structure and biological activity after denaturation. The natural IFN-α-2b used in the present invention was expressed in *E. coli*, with the expression condition and inclusion body washing conditions provided above. Three kinds of interferon obtained by washing were subjected to reduced SDS-PAGE, and the result is shown in FIG. 3. Single band appeared after staining with Commassie Brilliant Blue R-250 for the three kinds of interferon, indicating that the three kinds of interferon all have a certain extent of purity. However, based on the mobility of the band, the three kinds of interferon were even in the existence of the reduced SDS-PAGE electrophoresis, excessive SDS and mercaptoethanol-β. This difference was not due to the molecule weight the molecules, because the difference between three kinds of interferon is less than 3%, which was not sufficient to result in difference in SDS-PAGE analysis. Therefore, there were other obvious differences in properties (such as superficial nature and domain distribution of amine acids) among three kinds of interferon in addition to molecular weight. Non-reduced SDS-PAGE electrophoresis is the most commonly used method to determine whether the renatured protein have been revived to the natural three-dimensional structure. The correctly folded structure of protein is the most compacted, and its electrophoresis mobility is the maximum, thereby the efficiency of protein-renaturing could be evaluated. The denatured solution of the three kinds of interferon were renatured, then non-reduced SDS-PAGE was used to analyze the renatured sample, as shown in FIG. 4, 50% of the (consensus) interferon which have not been sequence-engineered maintains in non-natural status, while more than 90% of both interferon which have been sequence-engineered and natural interferon-α-2b are revived to natural status. This suggested that the variant IFN based on "INFERGEN™" could have the folding nature is comparable to the natural interferon after the sequence-engineering of amine acids. This leads to simpler production process and reduce cost.

Example 4

Purification of Product, and Removal of Mismatching Interferon

Figure 5:
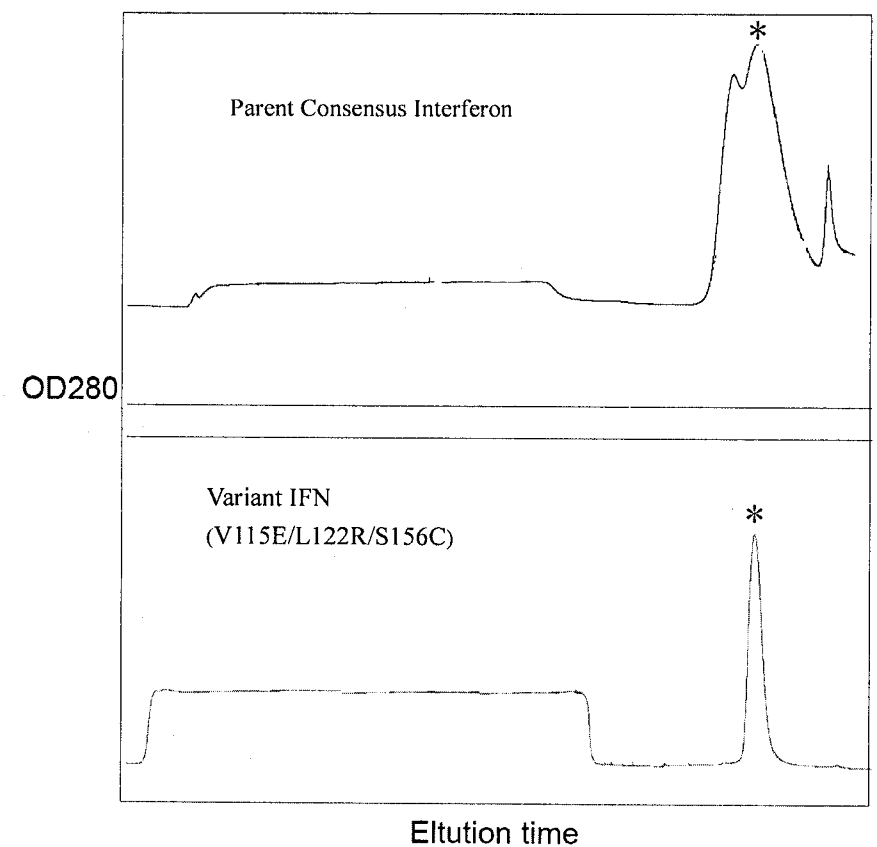
FIG. 5 shows the ion-exchange chromatography of folded interferon before and after sequence-engineering (A and B). The medium used is CM Sepharose Fast Flow (GE Healthcare Company), and the pH of buffer is 4.5. A saline gradient elution was used. The correctly folded interferon is marked with "*".

After renaturing, the interferon was purified through ion-exchange medium (CM Sephorose Fast Flow, GE Healthcare company) by taking advantage of the charge difference between the mismatched and correctly folding interferon. The ion-exchange chromatography map of the parent consensus interferon is shown in FIG., panel A. Two components appeared during the elution—they were determined to be mismatched interferon by non-reduced SDS-PAGE detection. Their mobility was smaller than that of the interferon properly folded. The ion-exchange chromatography map of the variant (V115E/L122R/S156C) is shown in FIG. 5, panel B. There was only one signal component and only one single band shown by non-reduced SDS-PAGE electrophoresis detection. It indicated that the variant IFN completely fold into proper three-dimensional structure.

Example 5

Study on Anti-Viral Activity

The anti-viral activity of consensus interferon INFERGEN™ developed by Amgen, the engineered new type of interferon conIFN and natural interferon-α-2b were investigated respectively. VSV virus could induce CPE in WISH cell. Pre-treatment with interferon could protect WISH cell from being disrupted by VSV virus, which is so called "experiment of cytopathic effect inhibition in WISH cell", the method is recorded in "Chinese Pharmacopoeia" (Third Edition). This is the commonly used cytopathic effect inhibition.

The result indicated that the activity of two variant IFNs (V115E/L122R and V115E/L122R/S156C) was comparable to the "INFERGEN™", and was even slightly higher than INFERGEN™. The variant interferon has higher anti-viral and anti-infection activity than the natural interferon-α-2b and the parent consensus interferon (see Table 1).

TABLE 1

Comparison result of anti-viral activity and folding nature

| | INFERGEN ™ | Interferon-α-2b | V115E/L122R | V115E/L122R/S156C |
|---|---|---|---|---|
| Anti-viral activity, U/mg | $2.80 \times 10^8$ | $1.11 \times 10^7$ | $3.78 \times 10^8$ | $5.44 \times 10^8$ |
| Folding nature, % | 50% | 90% | 50% | 90% |

What is claimed is:

1. An isolated variant consensus interferon protein comprising the amino acid sequence of SEQ ID NO: 5.

2. The variant consensus interferon protein of claim 1, further comprising at least one polyethylene glycol (PEG) moiety covalently attached to the protein.

3. The variant consensus interferon protein of claim 2, wherein said PEG moiety is attached at position 156 of the protein.

4. The variant consensus interferon protein of claim 2, wherein said PEG moiety is a PEG derivative.

5. A pharmaceutical composition comprising the variant consensus interferon protein according to claim 1 and a pharmaceutically acceptable excipient.

6. A method of suppressing viral activity in a subject, the method comprising administering to an animal or human subject a therapeutically effective amount of the pharmaceutical composition of claim 5.

* * * * *